(12) United States Patent
DeJongh

(10) Patent No.: US 11,717,237 B2
(45) Date of Patent: Aug. 8, 2023

(54) PROTON IMAGING SYSTEM INCORPORATING POSITRON EMISSION TOMOGRAPHY (PET) MODULES FOR OPTIMIZATION OF PROTON THERAPY

(71) Applicant: ProtonVDA LLC., Naperville, IL (US)

(72) Inventor: Don F. DeJongh, Naperville, IL (US)

(73) Assignee: ProtonVDA, LLC., Naperville, IL (US)

( * ) Notice: Subject to any disclaimer, the term of this patent is extended or adjusted under 35 U.S.C. 154(b) by 157 days.

(21) Appl. No.: 17/408,386

(22) Filed: Aug. 21, 2021

(65) Prior Publication Data
US 2022/0054096 A1 Feb. 24, 2022

Related U.S. Application Data

(60) Provisional application No. 63/068,580, filed on Aug. 21, 2020.

(51) Int. Cl.
*A61B 6/03* (2006.01)
*G01T 1/29* (2006.01)
*G06T 11/00* (2006.01)

(52) U.S. Cl.
CPC ............ *A61B 6/037* (2013.01); *G01T 1/2985* (2013.01); *G06T 11/006* (2013.01); *G06T 2207/10104* (2013.01); *G06T 2211/40* (2013.01)

(58) Field of Classification Search
None
See application file for complete search history.

(56) References Cited

U.S. PATENT DOCUMENTS 9,029,790 B2 * 5/2015 Yamaya ................. A61B 6/037
250/368
2019/0184197 A1 * 6/2019 Fallone ..................... A61N 5/10

* cited by examiner

*Primary Examiner* — Edwin C Gunberg
(74) *Attorney, Agent, or Firm* — Invent Capture, LLC.; Samuel S. Cho

(57) ABSTRACT

A novel proton imaging system incorporates positron emission detections to enhance proton therapy treatment preparation and procedural efficiencies while reducing operational costs associated with proton therapy. In one case, the novel proton imaging system incorporating a positron emission tomography (PET) module enables rapid on-the-fly in vivo range verification for proton therapy using position information from short-lived positron emitters produced during treatment. This unique in vivo range verification method produces more streamlined, accurate, and cost-effective results relative to conventional proton imaging systems. In another case, the novel proton imaging system incorporating the PET module provides a unique combinatory PET/pCT (proton computer tomography) scanning that creates more accurate maps for proton therapy planning for metabolically-active tumors. This proton imaging system also utilizes a novel concept of "virtual protons" originating from in vivo range verification measurements that mimic proton particle's characteristics for more accurate proton computer tomography (pCT) or computer tomography (CT).

17 Claims, 11 Drawing Sheets

PROTON BEAM

601A

VIRTUAL PROTONS

601B

100A

100B

1100

PROTON IMAGING SYSTEM INCORPORATING POSITRON EMISSION TOMOGRAPHY (PET) MODULES FOR OPTIMIZATION OF PROTON THERAPY

BACKGROUND OF THE INVENTION

The present invention generally relates to one or more medical imaging and treatment planning systems. More specifically, various embodiments of the present invention relate to novel utilizations of positron emission tomography (PET) in conjunction with a proton imaging system to improve speed, accuracy, and operating cost of proton therapy and corresponding treatment planning. Furthermore, various embodiments of the present invention also relate to methods of operating novel proton imaging systems that integrate and/or synergistically utilize PET modules for optimization of proton therapy or ion therapies. While most embodiments of the invention relate to imaging using protons and range verification of proton beams, the techniques can also be applied to imaging with ions such as helium, or treatment beams using ions such as carbon, in other embodiments of the invention.

In radiation therapy, protons provide more effective dose distributions compared to x rays, with a relatively low-dose deposition in the entrance region (i.e. also known as the "plateau"), followed by a steep increase to a dose peak (i.e. a Bragg peak) and an even steeper distal dose fall-off. This well-defined range is the main advantage of proton therapy, delivering less dose to healthy tissues, thus fewer complications and side effects and a better quality of life, even if the proton therapy does not necessarily exhibit an increased biological effectiveness relative to other available radiation therapies. However, the steep distal dose gradient and finite range of proton beams utilized in proton therapy can also be a significant disadvantage, when the actual position of proton beams is uncertain.

In a conventional proton therapy environment, such positional uncertainties may arise from a variety of factors. For instance, the conventional utilization of x-ray imaging for treatment planning to obtain a map of relative stopping power (RSP) of tissues (i.e. compared to water) may be inaccurate due to the differences in the dependence of x-ray attenuation and proton energy loss on tissue composition involving electron density and atomic number. This inaccurate mapping of tissue RSPs then results in an inherently-inaccurate conversion of x-ray Hounsfield units to proton RSP. Furthermore, positional uncertainties for proton therapy can also originate from the particularity of a patient setup (e.g. alignment of the patient to isocenter, deformations from non-rigid changes (e.g. shoulder movements)), an inadvertently-changed position of a tumor due to the patient's breathing cycle, a patient's anatomical changes during the course of fractionated treatments, or a combination thereof.

Conventional treatment planning procedures for proton therapy can take these uncertainties into account with mitigation measures, such as adding uncertainty margins, selecting beam angles tangential to organs at risk, and robust optimization. In addition, by utilizing additional dose delivery techniques such as Pencil Beam Scanning (PBS) and intensity modulation, the resulting treatment plans may become sufficiently robust to the uncertainties. However, these conventional mitigation measures inherently increase the high-dose treatment volume and can preclude use of the most advantageous beam angles. In order to improve the benefit-to-risk ratios of proton therapy while reducing related operational costs and diagnostics and treatment durations, additional innovations in the fields of proton beam-based image guidance and image reconstruction techniques may be advantageous. This is particularly the case for hypo-fractionated treatments who can benefit from more conformal dose distributions and a higher standard of safety during the high-dose delivery in each treatment.

Therefore, it may be desirable to devise a novel proton imaging system that incorporates and/or utilizes positron emission detection to enable rapid on-the-fly in vivo range verification for proton therapy using information from short-lived positron emitters produced during treatment.

Furthermore, it may also be desirable to devise a novel proton imaging system that incorporates and/or utilizes positron emission tomography (PET) modules to enable a unique combinatory PET/pCT (proton computer tomography) scanning that can provide more accurate maps for proton therapy planning for metabolically-active tumors.

In addition, it may also be desirable to devise a method for operating a novel proton imaging system that incorporates and/or utilizes PET modules to improve treatment preparation and procedural efficiencies while reducing operational costs associated with proton therapy.

SUMMARY

Summary and Abstract summarize some aspects of the present invention.

Simplifications or omissions may have been made to avoid obscuring the purpose of the Summary or the Abstract. These simplifications or omissions are not intended to limit the scope of the present invention.

In one embodiment of the invention, a method for operating a novel proton imaging system with positron emission tomography (PET) modules to enable rapid on-the-fly in vivo range verifications for proton therapy by utilizing information from short-lived positron emitters produced during a proton beam treatment is disclosed. This method comprises the steps of: (1) aligning a patient to an isocenter of a next proton beam treatment field in the novel proton imaging system; (2) transforming PET detector coordinates to isocenter coordinates, which are derived from diverging pencil beams and a time-of-flight (TOF) technique, wherein relative TOFs of two photons from a positron annihilation provide a measurement of annihilation positions along a line between the two photons; (3) tracking detectors and a target object in the patient aligned to the isocenter through native alignments provided by the novel proton imaging system (4) acquiring positron annihilation coincidence and TOF data from PET detector panels that detect positron emitters produced from a proton beam during treatment, wherein the positron annihilation coincidence and TOF data involves detection of secondary radiation from an interaction of the proton beam with the target object, which provides an opportunity for an in vivo range verification by detecting electron-positron annihilation events with scintillators in the PET detector panels; (5) executing gamma coincidence line and TOF-derived position probability density calculations in the isocenter coordinates in a scalable graphical processing unit (GPU) of the novel proton imaging system; (6) creating a treatment plan involving positions, timing, and gaps for delivery of pencil beams, a relative stopping power (RSP) map, and tissue composition information; (7) uploading the treatment plan to a real-time update of a treatment background model and a current pencil beam signal model executed in the scalable GPU or a central processing unit (CPU) of the novel proton imaging system, wherein the treatment background model and the current pencil beam signal model are configured to incorporate outputs of GPU calculations of the gamma coincidence line and the TOF-derived position probability density calculations dynamically in real time to enable real-time model refinements during the proton beam treatment; and (8) performing a fast range check before the next proton beam treatment field after taking account of the real-time model refinements to the treatment background model and the current pencil beam signal model.

In another embodiment of the invention, a method for operating a novel proton imaging system with positron emission tomography (PET) modules to enable a unique combinatory PET and pCT (proton computer tomography) scanning that provides more accurate maps for proton therapy planning for metabolically-active tumors is disclosed. This method comprises the steps of: (1) executing machine calculations in a scalable graphics processing unit (GPU) of the novel proton imaging system to transform PET detector coordinates to isocenter coordinates, which are derived from diverging pencil beams and a time-of-flight (TOF) technique, wherein relative TOFs of two photons from a positron annihilation provide a measurement of annihilation positions along a line between the two photons; (2) tracking detectors and a target object in a patient aligned to an isocenter through native alignments provided by the novel proton imaging system; (3) injecting isotopes to the patient for the unique combinatory PET and pCT scanning and aligning the patient to the isocenter; (4) projecting a proton beam and utilizing PET detector panels incorporated in the novel proton imaging system to detect positron emitters after the proton beam is projected on the target object in the patient, wherein the PET detector panels are rotated around the patient, or the patient is rotated around the PET detector panels during this image capture process to obtain a three-dimensional PET and pCT imaging information; (5) creating and inputting a low-intensity pencil beam delivery plan to the novel proton imaging system; (6) executing a computerized tomographic reconstruction of hybrid PET and pCT images in a singular isocentric coordinate system, wherein each of the hybrid PET and pCT images combines PET scanner image signatures with pCT image signatures to provide more accurate proton treatment planning maps for the metabolically-active tumors; and (7) displaying the hybrid PET and pCT images for proton treatment planning.

DETAILED DESCRIPTION

Figure 1A:
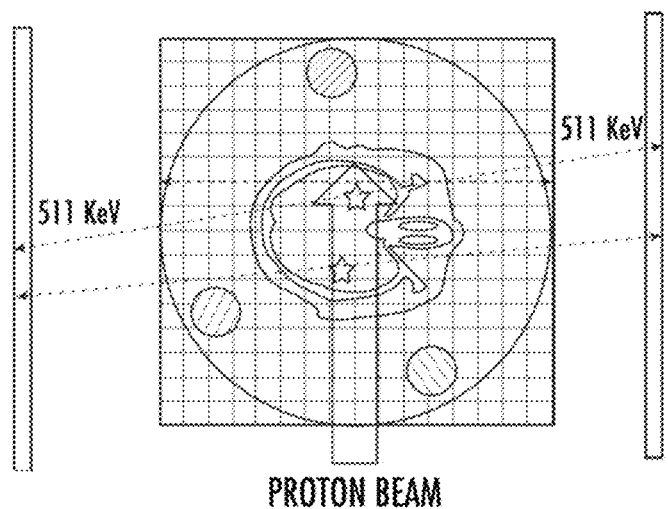
FIG. 1A shows positron emission tomography (PET) detectors transverse to proton beam for detection of coincident antiparallel 511 keV photon pairs during in vivo measurement, with an annihilation range given by the intersection of the antiparallel line with the pencil beam.

Specific embodiments of the invention will now be described in detail with reference to the accompanying figures. Like elements in the various figures are denoted by like reference numerals for consistency.

In the following detailed description of embodiments of the invention, numerous specific details are set forth in order to provide a more thorough understanding of the invention. However, it will be apparent to one of ordinary skill in the art that the invention may be practiced without these specific details. In other instances, well-known features have not been described in detail to avoid unnecessarily complicating the description.

The detailed description is presented largely in terms of description of shapes, configurations, and/or other symbolic representations that directly or indirectly resemble one or more novel proton imaging systems and related methods of operations that incorporate and/or utilize positron emission tomography to streamline treatment planning procedures and to improve speed, accuracy, and cost efficiency of proton therapy preparations and treatments. These descriptions and representations are the means used by those experienced or skilled in the art to most effectively convey the substance of their work to others skilled in the art.

Reference herein to "one embodiment" or "an embodiment" means that a particular feature, structure, or characteristic described in connection with the embodiment can be included in at least one embodiment of the invention. The appearances of the phrase "in one embodiment" in various places in the specification are not necessarily all referring to the same embodiment. Furthermore, separate or alternative embodiments are not necessarily mutually exclusive of other embodiments. Moreover, the order of blocks in process flowcharts or diagrams representing one or more embodiments of the invention does not inherently indicate any particular order nor imply any limitations in the invention.

For the purpose of describing the invention, a term herein referred to as "time-of-flight," or "TOF," is defined as the measurement of the time taken by an object or a particle to travel a distance through a medium. This measured TOF information can then be used to establish a targeted object's velocity, path length, or dynamic properties. In context of various embodiments of the present invention, TOF techniques are utilized to measure numerous positron annihilations on the targeted object (e.g. a patient's tumor targeted for proton therapy) over a defined interval, a collection of which can then be computed and analyzed to derive proton ray trajectories more accurately in the novel proton imaging system with integrated PET scanning capabilities. Specifically, the relative TOF of two photons from a positron annihilation provides a measurement of the position of the annihilation along a line between the two photons.

Furthermore, for the purpose of describing the invention, a term herein referred to as "pencil beam scanning," or "PBS," is defined as a precision dose-delivery technique that scans narrow proton particle beams across a target. Compared to using standard broad proton beams emitted by conventional proton therapy machines, the PBS may reduce unnecessary radiation exposure to unintended surrounding cells (e.g. non-cancerous cells near targeted tumor cells) through computer-guided precision beam steering.

In addition, a term herein referred to as a "virtual proton" is defined as a computer program-deduced and imaginary "proton-like" particle during PET scanning, which is configured to mimic proton particle's characteristics for more accurate proton computer tomography (pCT) or computer tomography (CT) image reconstructions, especially on thick parts of the patient undergoing proton therapy.

For example, a PET range measurement in accordance with an embodiment of the invention can provide information on the water-equivalent range along a path to an interior point in an object. The PET range measurements, when virtualized with proton-like characteristics in a computerized image reconstruction module executed by a novel proton imaging system, can supplement data used for a CT or a pCT image reconstruction on challenging beam angles (e.g. an excessively thick part of the patient).

One way to incorporate this information is by substitution of measured range in a proton beam with virtual protons, which can be conceptually utilized in iterative image improvement algorithms for CT or pCT reconstruction. Iterative algorithms adjust the RSP of each voxel so that the sums of the RSPs along the proton paths optimally match the energy lost by each proton. These algorithms can naturally incorporate the information from virtual protons, adjusting the RSPs of the voxels along the path of the proton beam to the stopping point of the proton beam to optimally match the total energy of the proton beam. In the preferred embodiment of the invention, the virtual protons have the water-equivalent range of the proton beam, the same geometrical stopping point of the proton beam as measured by the PET modules, a transverse distribution according to the pencil beam shape, and a number of virtual protons chosen to scale a typical proton precision to the precision of the PET range measurement. For instance, if the typical residual range uncertainty of a proton measured in the pCT system is 3 mm, and the PET range measurement has an uncertainty of 1 mm, a commensurate number of virtual protons to use would be $(3 \text{ mm}/1 \text{ mm})^2=9$.

One aspect of an embodiment of the present invention is providing a novel proton imaging system that incorporates and/or utilizes positron emission detections to enable rapid on-the-fly in vivo range verification for proton therapy using position information from short-lived positron emitters produced during treatment.

Another aspect of an embodiment of the present invention is providing a novel proton imaging system that incorporates and/or utilizes PET modules to enable a unique combinatory PET/pCT (proton computer tomography) scanning that can provide more accurate maps for proton therapy planning for metabolically-active tumors.

Yet another aspect of an embodiment of the present invention is providing a method for operating a novel proton imaging system that incorporates and/or utilizes PET modules to improve treatment preparation and procedural efficiencies while reducing operational costs associated with proton therapy.

Various embodiments of the present invention describing a novel proton imaging system are intended to improve proton therapy in at least three major areas: (1) in vivo range verification during proton beam treatment with additional information provided by PET modules for more streamlined, accurate, and cost-effective results, and (2) enhanced imaging for treatment planning from combinatory PET/pCT image reconstructions and (3) "virtual protons" originating from in vivo range verification measurements that mimic proton particle's characteristics for more accurate proton computer tomography (pCT) or computer tomography (CT).

In the preferred embodiment of the invention, the proton imaging system is capable of both proton radiography (pRad) and proton CT (pCT), while additionally integrating and/or utilizing PET modules for enhanced target detection accuracies and synthetic hybrid PET/pCT image reconstructions. Range uncertainties can be reduced with pCT, or alternatively dual-energy CT (DECT), while pRad is intended to provide a fast and efficient check of patient set up and integrated range along a beam's eye view just before the proton beam treatment. The detection of secondary radiation from the interaction of a proton treatment beam with the target (e.g. a tumor) provides an opportunity for in vivo range verification by detecting electron-positron annihilation events with scintillators in PET detection modules during the proton beam treatment procedure. Such in vivo range verification techniques may be particularly useful in hypofractionation because the greater number of treatment protons produces a larger signal of secondary radiation.

Observations of $^{12}N$ positron emitters copiously produced in a proton scanning pencil beam by interactions of protons with $^{12}C$ have brought the PET technique to the forefront of promising in vivo range verification techniques. With an 11 msec half-life, the $^{12}N$ signal can be detected promptly during a short beam-off period after a proton pulse. These experiments, using 20×20 cm² PET detector panels, have demonstrated range sensitivity on PMMA targets of 2.7 mm with $10^8$ protons/pulse and 0.9 mm with $10^9$ protons/pulse. In comparison, delivering a 5 Gy dose to a 10 g volume requires of order $10^{10}$ protons. With a threshold of 21 MeV, a peak at 25 MeV and a plateau above 48 MeV, the cross-section for $^{12}N$ production has a favorable distribution, falling to zero just ~0.5 cm before the proton stopping point.

FIG. 1A shows a diagram (100A) of positron emission tomography (PET) detectors, which are positioned transverse to proton beam for detection of coincident antiparallel 511 keV photon pairs in vivo measurement, with an annihilation range given by the intersection of the antiparallel line with the pencil beam. In addition, FIG. 1B shows a second diagram (100B) of PET detectors that are transverse to proton beam for detection of coincident antiparallel 511 keV photon pairs originating from an injected substance, while simultaneously operating a low-intensity imaging beam for pCT imaging, wherein detectors and proton beam rotate around the object, or the object rotates within fixed detectors and beam, to enable both pCT and PET voxel grid image reconstructions.

Figure 1B:
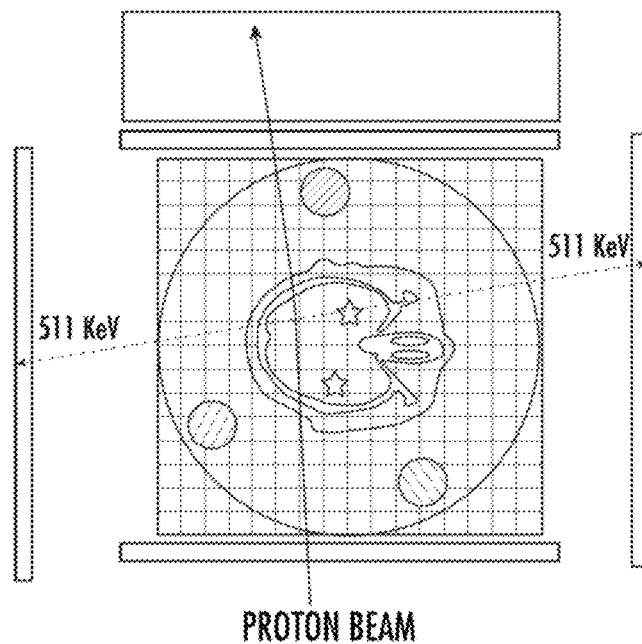
FIG. 1B shows PET detectors transverse to proton beam for detection of coincident antiparallel 511 keV photon pairs originating from an injected substance, while simultaneously operating a low-intensity imaging beam for pCT imaging, wherein detectors and proton beam rotate around the object, or the object rotates within fixed detectors and beam, to enable both pCT and PET voxel grid image reconstructions.

As illustrated in these two diagrams (100A, 100B) in FIGS. 1A and 1B, the PET detection provides a straightforward determination of the position of the positron annihilation along the pencil beam axis. One drawback is the relatively large positron energy in $^{12}N$ decays, leading to a large range of the positrons (e.g. 1.8 cm (root-mean-square)). This large range of positrons in decay can cause extended smearing, instead of sharp distributions.

Figure 2:
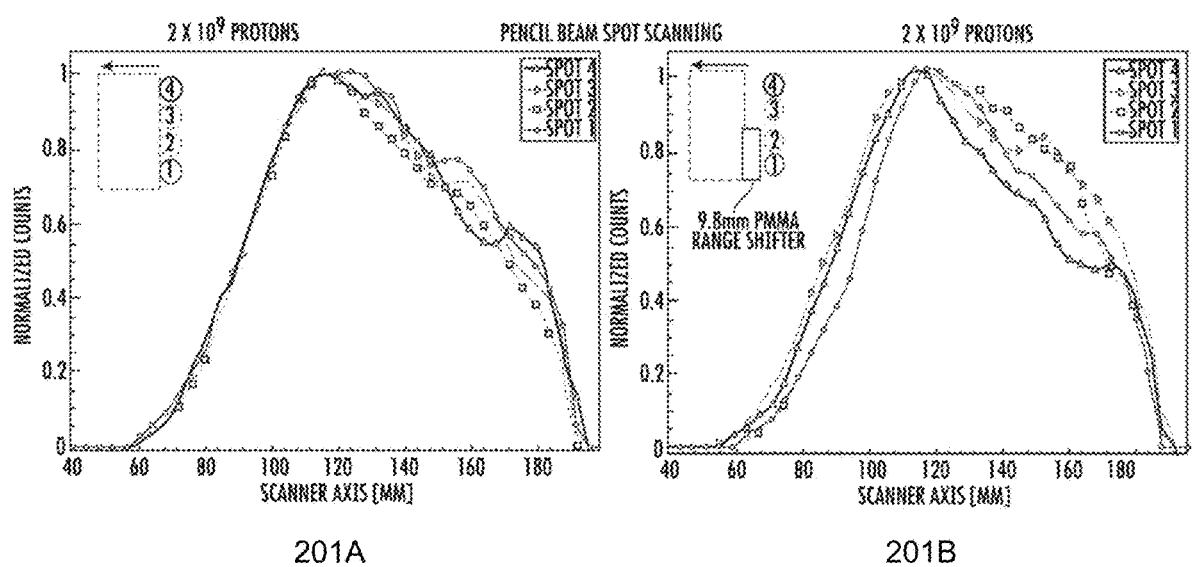
FIG. 2 shows an example of measured range distribution of positron annihilations, wherein the proton direction is from the right to the left, and the beam stopping point information is given by the left edge of the distributions revealing a clear shift in the presence of a 9.8 mm range shifter for two of the spots.

However, there may be novel remedies to this drawback in PET detection methods. In particular, FIG. 2 shows an example of measured range distribution of positron annihilations in two diagrams (201A, 201B). The proton direction in each diagram is illustrated as moving from the right to the left, and the beam stopping point information is given by the left edge of the distributions, which reveals a clear shift in the presence of a 9.8 mm range shifter for two of the spots. As shown in these two diagrams (201A, 201B) in FIG. 2, range shifts are visible as shifts of the distribution. Although inhomogeneities and composition variations in patients can make prediction of the shape and an absolute range determination difficult, the comparison of distributions between treatment fractions may be able to enhance the quality of computerized image reconstruction by utilizing the PET detection methods in proton therapy.

Therefore, various embodiments of the present invention disclose a novel proton imaging system incorporating and/or utilizing positron emission tomography (PET) scanning modules and related methods of operation for clinical use in proton therapy treatment rooms. These embodiments of the present invention provide two important and advantageous applications for proton therapy optimization. The first application of the novel proton imaging system, as disclosed in various embodiments of the present invention, is in on-the-fly in vivo range verification that utilizes short-lived positron emitters produced during a proton beam treatment step. The PET detection approach provides important advantages over conventional methods of range verifications that exploited either longer-lived positron emitters or a prompt gamma signal. The second application of the novel proton imaging system, as also disclosed in various embodiments of the present invention, is in hybrid PET/pCT (hybrid positron emission tomography and proton CT) scanning, which combines the PET scanner image signatures with the pCT image signatures to provide more accurate proton treatment planning maps for metabolically-active tumors.

In the preferred embodiment of the invention, the novel proton imaging system with PET scanning modules provide in vivo range verification with $^{12}N$ signals, which has some major advantages over conventional range verification methods using the prompt gamma. The novel proton imaging system with PET scanning modules can be constructed as relatively light and compact panels, in contrast to conventional prompt gamma-based systems that typically require massive collimators, large detector volumes, large enclosures, and large mounting systems.

The large $^{12}N$ signal and the simplicity of the range reconstruction analysis enable streamlined and rapid on-the-fly range verification (i.e. also called herein interchangeably as the "range check"), which is more useful than conventional after-the-process confirmation. For instance, by utilizing the novel proton imaging system with PET scanning modules, the in vivo range verification with $^{12}N$ signals can pause a treatment process after 10 percent or less of the scheduled dose is delivered for tumors as small as 10 grams, and the range check result can be delivered within a fraction of a second. In case of any serious discrepancy found during the in vivo range verification, the proton beam treatment can be aborted before most of the dose is delivered. If the range check raises any questions, it may be desirable to continue the pause for periods of seconds or minutes to collect additional data before making a decision to resume treatment, or to obtain further diagnostics in case of a decision to abort. For example, the oxygen content of a tumor sometimes changes over the course of radiation therapy, and this can affect the range distributions or the choice of optimal treatment plan. A longer pause to observe different longer-lived isotopes produced on carbon and oxygen targets can provide information on the oxygen content.

It should be noted that PET/CT scans, using molecules such as fluorodeoxyglucose (FDG) that incorporate the $^{18}F$ positron emitter, are useful in diagnosis, target delineation, treatment planning, and assessment of tumor responses. Ongoing advances in PET/CT scanning technology provide a rich data set on tumor metabolism and contribute to increasingly precise and personalized radiation therapy. Although conventional standalone diagnostic PET/CT machines (i.e. typically located in a separate room away from proton scanning and treatment machines) may be used disjointedly and non-synergistically for certain radiation therapies, such conventional PET/CT machines are unable to provide more accurate, synergistic, PET/pCT hybrid image reconstruction synthesized by the novel proton imaging system of the present invention that directly incorporates PET scanning modules.

For example, the PET/pCT hybrid scan provides more accurate information for treatment planning because PET activity is directly located within the relative stopping power (RSP) map, with no need for deformable image registration of the diagnostic image. With the growing interest in treating patients in the seated position, the removal of the necessity of the deformable image registration of the diagnostic image is particularly advantageous in enabling the proton imaging system with PET modules (i.e. a PET/pCT system) to be constructed for both horizontal and vertical positioning. Furthermore, the utilization of a scalable number of graphics processing units (GPUs) for PET/pCT image data acquisitions and reconstructions in the novel proton imaging system with PET modules provide quicker turnaround time for repeated imaging during patient diagnosis, thus enabling examination of different metabolic pathways at different stages of the proton beam treatment, unlike conventional solutions.

Furthermore, it should also be noted that elapsed time per patient in a proton therapy treatment room carries precious value from an operational standpoint, as it essentially bottlenecks the total number of treatable patients per day in the treatment room filled with expensive imaging and radiation therapy equipment. The novel proton imaging system with PET scanning modules provides time-of-flight (TOF) PET scanning that reduces imaging time by constraining the position of each positron annihilation. Some conventional PET/CT scanners are capable of achieving timing resolution of 210 ps in the clinic, which results in scan times below 10 minutes with reduced administered dose. The novel proton imaging system with PET scanning modules in various embodiments of the present invention is able to achieve even better performance with as timing resolutions improve, for example, to 170 psec full width at half maximum (FWHM), which corresponds to a 2.5 cm spatial interval.

Because the PET panels in a PET/pCT system are unable to cover as much solid angle as PET/CT, an equivalent image may take more time to acquire compared to PET/CT systems, but additional strategies, such as administering a higher activity dose or interpolating from a previously-cached PET/CT image to reduce the amount of data analysis and graphical generation, may accelerate PET/pCT hybrid image reconstruction speed even further. Furthermore, potential challenges associated with patient-related motion management in the novel proton imaging system with PET scanning modules may be alleviated by mapping the tumor location throughout the breathing cycle. Since a pCT scan requires only a few minutes of beam time and a few mGy of dose, a longer PET/pCT scan is able to provide more detailed information throughout the breathing cycle at a safe dose. This motion management technique, whether based on respiratory gating or tumor tracking, can then make use of detailed information on tumor position in the 3D RSP map as a function of the patient's breathing phase.

Figure 3:
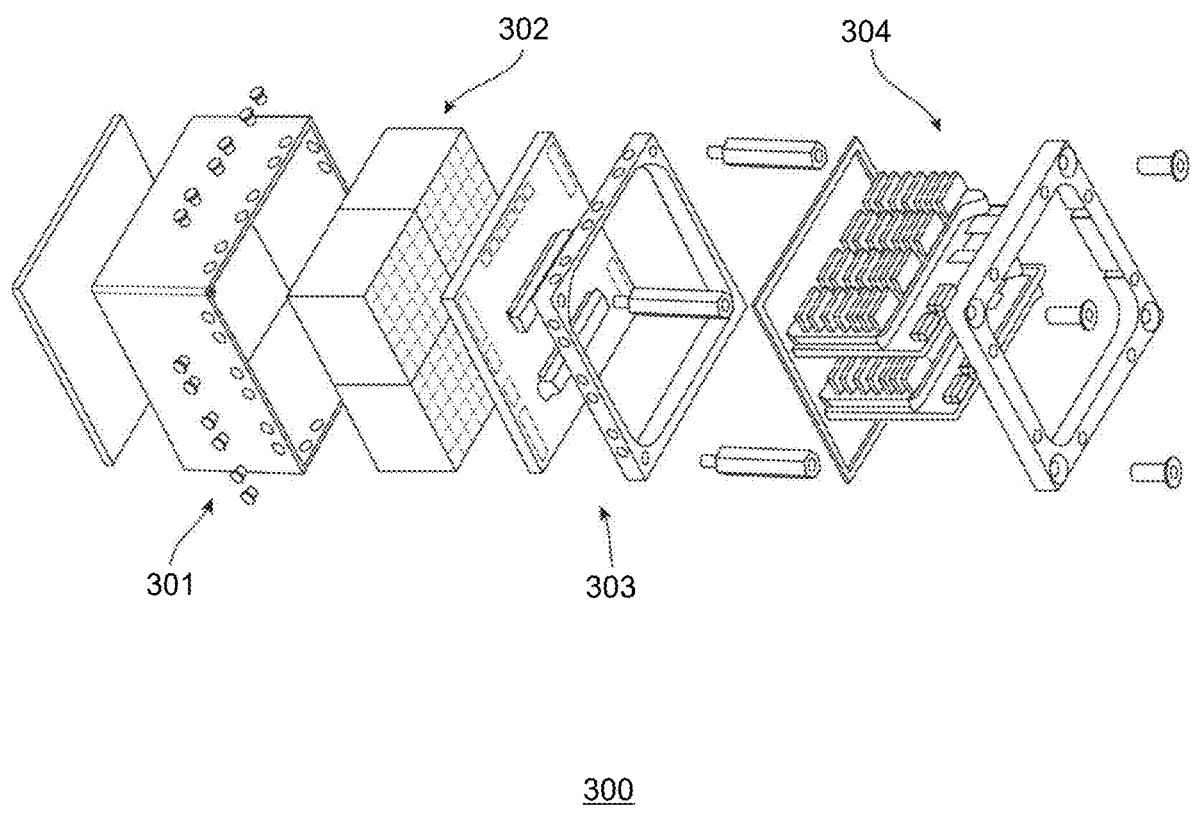
FIG. 3 shows an exploded view of a PET module with scintillator crystals measuring $3\times3\times20$ cm$^3$ arranged in a $16\times16$ array, wherein each crystal is individually read out with a Multi-Pixel Photon Counter (MPPC).

The novel proton imaging system disclosed herein provides synergy in patient tumor location and condition status detections, on-the-fly range verification during proton beam treatments, and hybrid PET/pCT images through a novel image reconstruction module executed on a scalable number of GPUs and CPU cores. As a case in point, FIG. 3 shows an exploded view of a PET module (300) with scintillator crystals (302) measuring 3×3×20 mm$^3$ arranged in a 16×16 array, wherein each crystal is individually read out with a Multi-Pixel Photon Counter (MPPC) (303) and further processed by a signal processor (304). These components may be enclosed in a PET module case (301), which is preferably also physically further integrated into the novel proton imaging system itself.

In another embodiment of the invention, the PET module (300) may be a standalone apparatus but operatively connected to the novel proton imaging system through an electrical or optical connection to function as a component of the uniquely-integrated PET/pCT system architecture provided by the novel proton imaging system. As illustrated in FIG. 3, the PET module (300) integrates the scintillator crystals (302), the MPPC array (i.e. photo sensors) (303), and the signal processor (304), and further provides field programmable gate array (FPGA)-based data formatting for PET data outputs to the rest of the novel PET/pCT imaging system. In the preferred embodiment of the invention, available clock, power, and relay boards that are typically also integrated into the PET module (300) allow the novel PET/pCT imaging system to add a scalable number of other PET modules that provide data acquisition (DAQ) into a memory unit of the novel image reconstruction module, which is executed on a scalable number of GPUs and CPU cores of the system.

Figure 4:
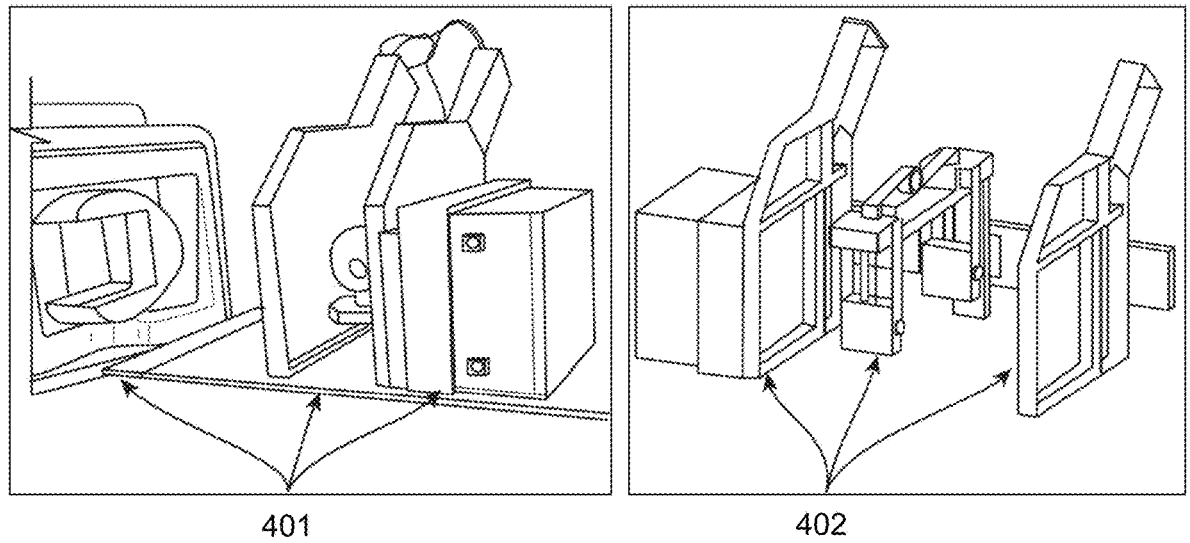
FIG. 4 shows a proton imaging system incorporating PET modules between two separation-adjustable tracking planes to receive a proton beam with head phantom between the two tracking planes, and a pCT sample image synthesized from the system, in accordance with an embodiment of the invention.

FIG. 4 shows an illustration (400) of a novel proton imaging system (401, 402) incorporating PET modules between two separation-adjustable tracking planes to receive a proton beam with head phantom between the two tracking planes, and a pCT sample image (403) synthesized from the system, in accordance with an embodiment of the invention. In the preferred embodiment of the invention, positron emissions are detected as a coincidence between two gammas in detectors arranged on opposite sides of the target object.

In one example of utilizing this novel proton imaging system (401, 402), each gamma has a time stamp, and the coincidence resolving time (CRT) is 170 ps (FWHM) and each PET module has a 1 MHz event rate capability. In one operational mode, the count rate of single gammas can provide $7.7 \times 10^{-4}$/proton with the beam on, and $10^9$ protons can realistically yield less than one million gammas. An individual 5×5 cm$^2$ module may have a fraction of the solid angle and is configured to easily handle the event rate for a 1 nA proton beam. Because the novel proton imaging system (401, 402) is designed to provide pencil beam scanning (PBS), a beam spot with a particular range and steering can be programmed to dwell until a prescribed dose is delivered, and the beam can then be turned off for a programmable length of time while the steering is adjusted for the next spot. For the purpose of acquiring $^{12}$N data, the gaps between spots can be a few half-lives or a few×11 msec. In a clinical implementation, a pause in dose delivery after an initial number of spots could provide time for the in vivo range verification. If a serious discrepancy is detected during the in vivo range verification, the proton treatment could be halted before most of the dose is delivered. Otherwise, the planned proton PBS treatment procedure may be continued with no further gaps.

Furthermore, the novel proton imaging system (401, 402) can coordinate data acquisition (DAQ) with a pencil beam scanning (PBS) component, which is followed by a scalable GPU-based fast automatic image processing in an image reconstruction module. Similarly, the PET module in the novel proton imaging system (401, 402) is also configured to utilize the scalable GPU-based fast automatic image processing in the image reconstruction module. The reconstruction of the in vivo range distribution uses knowledge of the planned proton beam scanning pattern. For example, the start of the scan can be recognized in the PET data from the start of a high event rate. The time stamp of each individual gamma then determines its assignment to a particular beam spot, either to the beam-on time or to the beam-off gap after the spot. Positron annihilations are identified as coincidences between gammas, and the range reconstruction, as previously illustrated in FIG. 1, makes use of the known beam spot position to find the intersection of the line between the two gammas with the beam.

For various embodiments of the present invention, scalable GPU processing is highly effective for parallel processing of numerous image reconstruction events with the same instruction set. In one example of proton imaging, the novel proton imaging system (401, 402) can process 3.5 million protons in five seconds with a single GPU card and find the intersection of each proton with approximately 200 voxels. With this performance parameter, it can be estimated that approximately $3 \times 10^4$ coincidences are needed for a 1 mm range precision. The image processing will require assigning gammas to spots, finding coincidences for gammas in the gaps, and finding a range for each coincidence. Given the relatively low number of events and the simplicity of the analysis, the novel proton imaging system (401, 402) in this example can complete the range verification analysis during a proton therapy in a fraction of a second as long as data transfer operations are also optimized for rapid processing by the system.

The pCT sample image (403) synthesized from the system is taken from a target sample (e.g. a pork shoulder and rib), which was rotating in a horizontal beam line with stationary detectors. The pCT sample image (403) was reconstructed in the voxel grid rotating with the object. With the addition of PET panels providing data in the same voxel grid, and the pCT image providing an ideal attenuation correction, a PET/pCT image can be obtained. Any noise from the PET isotope in the novel proton imaging system (401, 402) is typically negligible from the tracking detectors because the interaction length of 511 keV gammas in plastic scintillator is roughly 10 cm, and any increased noise in the residual range measurements is also minor from occasional overlap with a 0.5 MeV gamma, compared to the 50 to 100 MeV energy typically carried by stopping protons.

By tracking protons from a PBS system with known steering, the novel proton imaging system (401, 402) can directly transform proton trajectories (i.e. as illustrated in FIG. 1) into isocenter coordinates, which is a unique and elegant method to register the reconstructed images (e.g. PET/pCT hybrid images) with the treatment isocenter. Preferably, the novel proton imaging system (401, 402) also integrates optical tracking to measure movements of detectors and objects, which in turn provides an external reference for registration. It should be noted that methods to register images in prior art in vivo range check systems have commonly exhibited registration errors, and a shift in the positioning of the prior art systems along the beam axis often appeared as a range error. Contrary to the prior art systems, the novel proton imaging system (401, 402) utilizes calibration techniques with point sources, aligned to isocenter with laser systems to accommodate registration of the PET system with isocenter. Imaging of the point sources simultaneously with the proton imaging system can provide another check by co-registration of PET images from the PET module and pCT images from the novel proton imaging system (401, 402). In addition, a clever use of the PBS system can contribute to the registration of the PET images. For example, the average TOF interval of many positron annihilations vs. range in a uniform phantom can determine the ray of the pencil beam in FIG. 1 to high precision.

Figure 5:
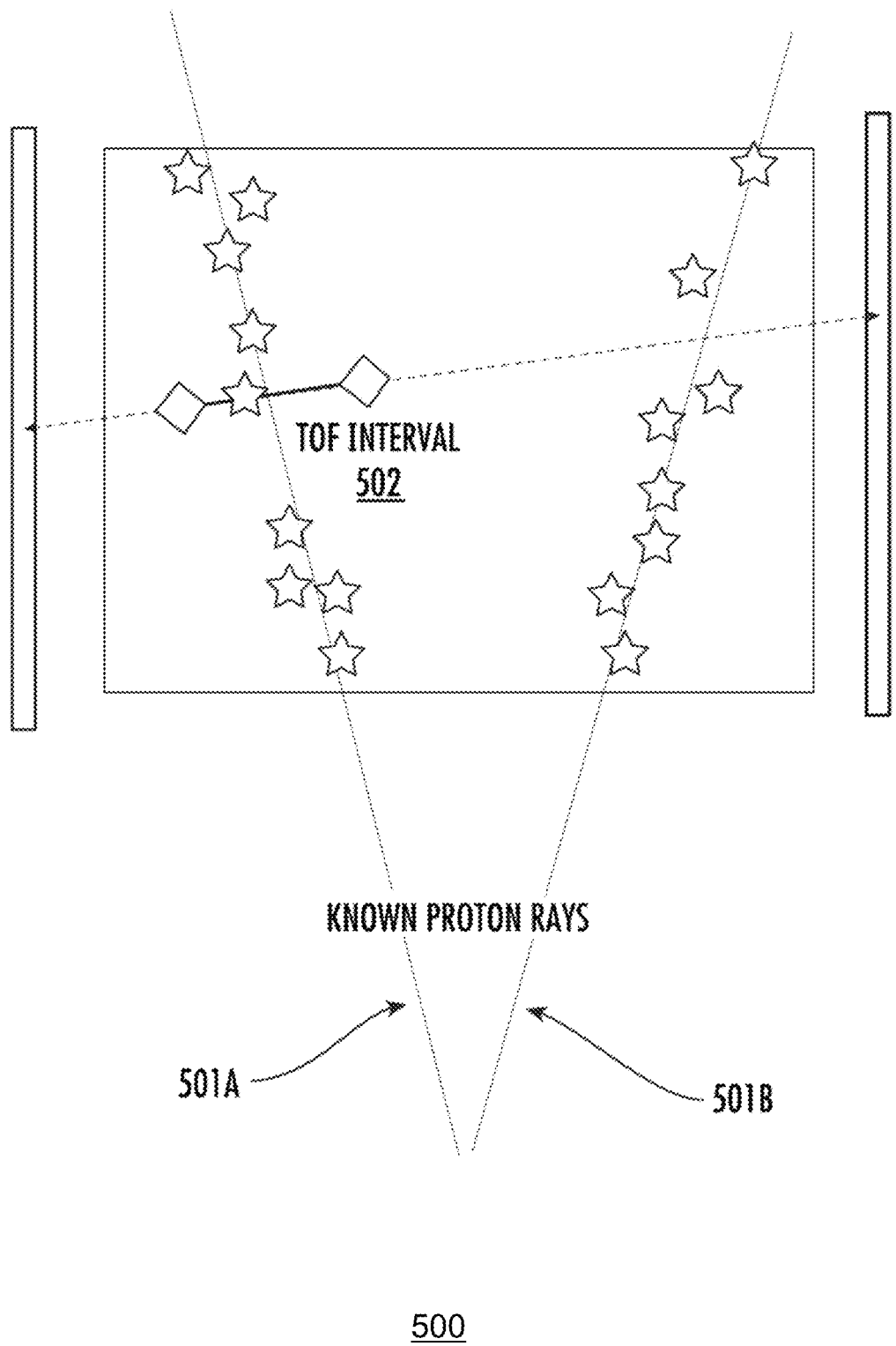
FIG. 5 shows a diagram showing diverging proton rays from the proton imaging system that produces positron annihilations in a target, where TOF intervals from numerous annihilations are combined to determine the proton ray trajectories in the PET system, in accordance with an embodiment of the invention.

FIG. 5 shows a diagram (500) showing diverging proton rays (501A, 501B) from the proton imaging system that produces positron annihilations in a target, where TOF intervals (502) from numerous annihilations are combined to determine the proton ray trajectories in the PET system, in accordance with an embodiment of the invention. Because off-axis pencil beams (i.e. 501A, 501B) diverge along the beam direction, the diversion provides a determination of the PET system positioning along the beam axis, as shown in FIG. 5. The PET system positioning determination procedure can provide alignment and quality assurance using internal data only, without relying on external alignment marks on the enclosure, alignment of the target to isocenter, or knowledge of the stopping power of the target.

In the preferred embodiment of the invention, the PET system positioning determination procedure involves the following eight steps:

(1) Prepare survey and positioning parameters;

(2) Three rotational and three translational parameters for each of the two planes (or possibly one set for a number of sub-assemblies in the enclosure) that have starting values are used to convert internal detector coordinates to isocenter coordinates;

(3) Place material block around isocenter. Utilize Teflon, graphite, or other suitable substance for the material, because the larger density (e.g. 2.2 g/cc) reduces positron diffusion. A precise positioning or proton range is not required at this juncture, as long as proton rays will be present;

(4) Deliver a set of pencil beams with known steering to the isocenter plane and known directions as diverging rays from the focal point;

(5) Pencil beam width and positron diffusion define a Gaussian distribution for positron annihilation;

(6) For each gamma coincidence, draw line between gamma hits and find the probability density of the position of the positron annihilation. Hit resolution specifies a Gaussian uncertainty transverse to line. TOF resolution specifies a Gaussian uncertainty along the line;

(7) For each gamma coincidence, calculate a $\chi^2$ of the overlap between the pencil beam and the coincidence line. Sum $\chi^2$ of all the coincidences;

(8) Using standard techniques, find the rotational and translational parameters that minimize $\chi^2$.

Figure 6:
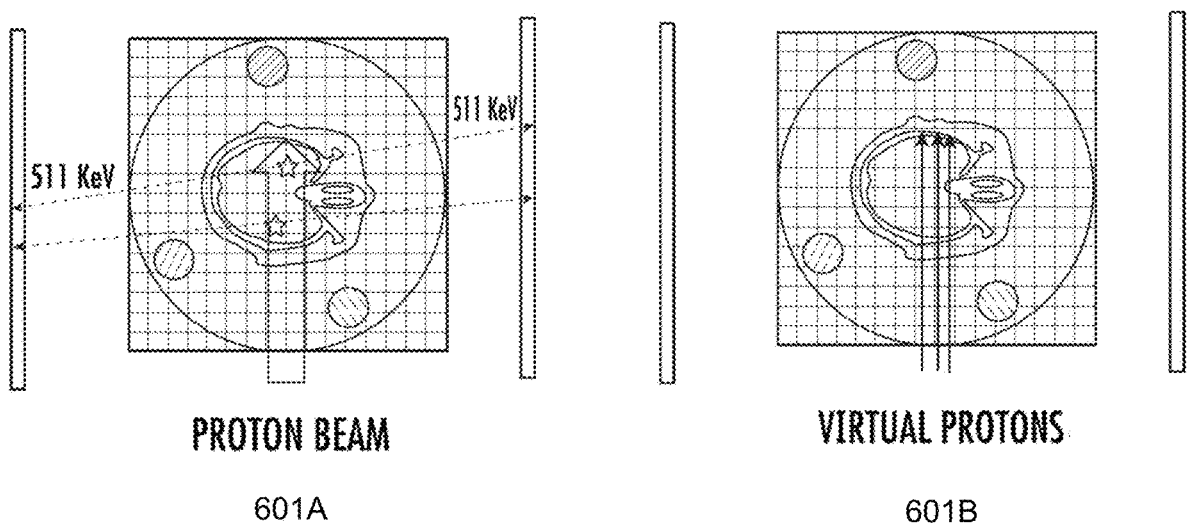
FIG. 6 shows a novel substitution for a measured range in a proton beam with virtual protons utilized in iterative computerized imaging algorithms to improve CT or pCT image reconstruction, in accordance with an embodiment of the invention.

FIG. 6 shows a diagram (600) of a novel substitution for a measured range in a proton beam (601A) with virtual protons (601B) utilized in iterative computerized imaging algorithms to improve CT or pCT image reconstruction, in accordance with an embodiment of the invention. In this diagram (600), a PET range measurement provides information on the water-equivalent range along a path to an interior point in an object. This PET range measurement can supplement data used for a CT or a pCT reconstruction. For example, pCT uses protons transmitted through a patient, and the patient may be too thick in some directions. In such situations, the PET range measurement method may provide information along these directions to provide more accurate range parameters. One way to incorporate this information is by substitution of measured range in a proton beam with virtual protons (i.e. 601B) for use in iterative algorithms, which in turn improve CT or pCT image reconstructions. Iterative algorithms adjust the RSP of each voxel so that the sums of the RSPs along the proton paths optimally match the energy lost by each proton. These algorithms can naturally incorporate the information from virtual protons, adjusting the RSPs of the voxels along the path of the proton beam to the stopping point of the proton beam to optimally match the total energy of the proton beam.

In the preferred embodiment of the invention, the virtual protons (601B) have the water-equivalent range of the proton beam, the same geometrical stopping point of the proton beam as measured by the PET system, a transverse distribution according to the pencil beam shape, and a number of virtual protons chosen to scale a typical proton precision to the precision of the PET range measurement. For example, if the typical residual range uncertainty of a proton measured in the novel proton imaging system is 3 mm, and the PET range measurement has an uncertainty of 1 mm, a commensurate number of virtual protons to use would be $(3 \text{ mm}/1 \text{ mm})^2=9$.

Figure 7:
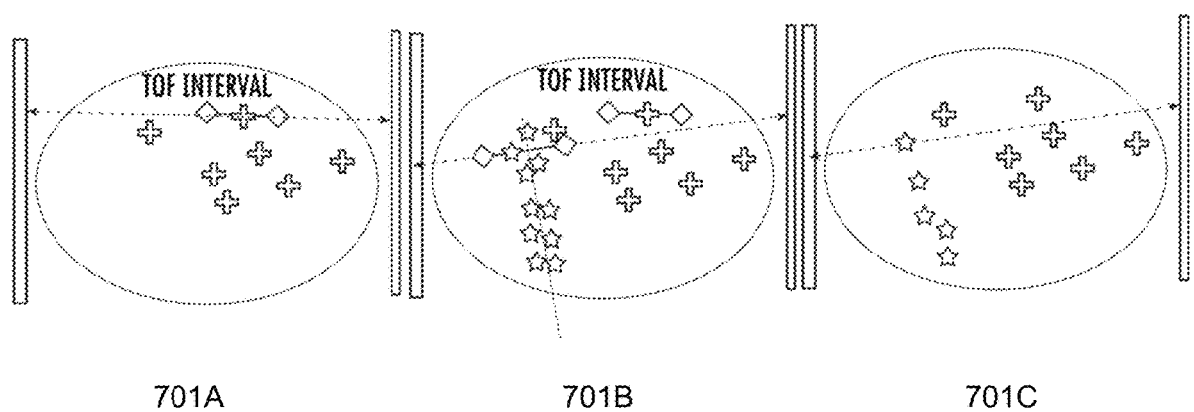
FIG. 7 shows a novel method for a quick range check during an iterative proton treatment that utilizes TOF interval measurements to map out the spatial distribution of this background before the new treatment field starts and to distinguish the signal from the new pencil beam, in accordance with an embodiment of the invention.

As the treatment progresses, longer-lived isotopes also produced in the proton beam accumulate, producing a sustained signal and potentially a background to the signal from short-lived isotopes. Treatments usually require more than one treatment fields, and range verification for one field may be subject to backgrounds from a previous field. FIG. 7 shows a novel method (700) for a quick range check during an iterative proton treatment that utilizes TOF interval measurements to map out the spatial distribution of this background before the new treatment field starts and to distinguish the signal from the new pencil beam, in accordance with an embodiment of the invention. In a first step (701A), long-lived positron emitters are present from a previous treatment field, which can be measured and tracked accurately with TOF interval measurements and analysis by the novel proton imaging system with the PET scanning module. Then, during the current stage of treatment as a second step (701B), a proton beam (i.e. a treatment beam) produces short-lived positron emitters, and all positron emitters present in the current treatment field can be measured and tracked accurately with TOF interval measurements and analysis. Subsequently, in a third step (701C), short-lived positron signals are partly decayed away one half-life after the treatment beam ends, and the changes in the presence of the remaining positron emitters are also measured and tracked accurately with TOF interval measurements and analysis in preparation for the next treatment field.

As shown in the novel method (700) in FIG. 7, the TOF capability is utilized to assist an accurate mapping of the spatial distribution of the background (e.g. a previous treatment field) before the new treatment field starts, and also to distinguish the residual signal from the new pencil beam. The time dependence of this background can also be studied since it will be composed of a combination of isotopes with different half-lives. In addition, the short-lived signal appears as an excess over the sustained background that decays with the characteristic 11 msec half-life. For each gamma coincidence, it is possible to draw a line between gamma hits and derive a probability density of the position of the positron annihilation. The hit resolution specifies a Gaussian uncertainty transverse to line. TOF resolution specifies a Gaussian uncertainty along the line. The combined probability densities of all the measured gamma coincidences can be fit to a model of the signal and background, with signal fraction and proton stopping point as the fit parameters. The background model can be determined from data as described above just before the treatment, and the model for the signal can be determined from a simulation of the proton beam using the treatment planning RSP map along with assumptions of the carbon content of the various tissues. The simulation can incorporate TOF resolution, pencil beam width, and diffusion distance of the positrons.

The fast range check or verification at the start of the treatment is quite straightforward, because the backgrounds should be relatively low and relatively well-determined from data just before the start of treatment. The signal may comprise a single applied pencil beam in one embodiment, or a plurality of pencil beams in another embodiment, which are aimed at the distal edge of the treatment field. In some instances, PET data taken during the entire treatment can be further utilized in a programmed dose delivery via time correlation with known pencil beam locations, the use of positional probability densities, and models of the signal from the current pencil beam and backgrounds from previous pencil beams. In one example, proton beams deliver protons in bunches with a wide variety of time structures, with bunch repetition rates over 100 MHz for cyclotrons and typically 1 KHz for synchro-cyclotrons. Prompt gammas can be rejected from their coincidence with proton bunches, while positron annihilations can be observed either in a gap in dose delivery or during dose delivery, which is generally not coincident with proton bunches.

The result from this method (700) executed on the novel proton imaging system with PET scanning modules is a rich dataset providing information on the delivered dose distribution, proton stopping power distribution, and the tissue composition distribution used for the signal model. Although PET techniques are applied in this embodiment of the invention, the analysis in this circumstance is typically not tomographic. Instead, the positrons observed from individual pencil beams and individual gaps between pencil beams are utilized. The novel method (700) in FIG. 7 utilizes the TOF to fit the data to the signal and background components but the dose distribution can be assigned from the known pencil beam profile, and the derived dose distribution is not limited by the TOF resolution. In contrast, conventional prior art attempts to verify range and dose distribution using PET isotopes relied on a single time-integrated tomographic image acquisition after the end of treatment. This produced workflow problems since the sophisticated imaging process requires extra time and clinical effort in the treatment room. In addition, the resulting image produced intensity distributions that were difficult to interpret, due to effects such as biological washout as the isotopes circulate and decay within the body over time, depending on the length of the delay before imaging. The total dose distribution for the treatment is the sum of the dose distributions from all the individual pencil beams. Each individual pencil beam in turn is considered as the source of the signal, with the background determined by the data taken up to the time of that pencil beam, and the fit is performed for the individual pencil beam. The dose for the individual pencil beam is assigned from the known dose profile for that pencil beam. At the end of the treatment, the total dose distribution can be compared to the prescribed dose distribution.

In addition to the $^{12}$N produced by protons interacting with carbon, many positron emitting isotopes are produced, all with longer half-lives. Therefore, the background fraction generally increases as the treatment progresses. In the preferred embodiment of the invention, some of the most important include:

Isotopes produced in bone
  $^{29}$P, produced on Phosphorus, 4.1 sec half-life
  $^{38m}$K, produced on Calcium, 0.92 sec half-life
Isotopes produced on Carbon
  $^{11}$C, 122 sec half-life
Isotopes produced on Oxygen
  $^{15}$O, 1223 sec half-life The isotope production and positron annihilation distribution can be predicted using known production rates and positron diffusion distances combined with the pencil beam size, the RSP map used for treatment planning, and additional assumptions on tissue composition. Signal and background distributions can be continuously updated with information from the plan for pencil beam steering and dose, as well as the decay times of the various isotopes. Requiring consistency with data will further constrain these models. Programmed gaps in the dose delivery can potentially provide useful information. Many systems require gaps of a few seconds while changing proton energy, and the time dependence during these gaps will constrain models of isotope distributions. Data from a few minutes of measurements after the end of treatment could provide similar constraints.

For example, uncertainties in tissue composition could affect the shape of the signal distributions, which in turn can affect the accuracy of the range check. Discrepancies in the assumed compositions could show up as discrepancies in the measured distributions of different isotopes. While positrons from $^{12}$N have an 18 mm diffusion length in water, positrons from other isotopes have diffusion lengths of 5 mm or less and thus can provide more fine-grained information. This information can be used to update the composition assumptions and produce more accurate range checks for subsequent treatment fractions. The dose distribution map from analysis of the entire data set can be compared with the prescribed dose distribution. In case of discrepancy, the method of virtual protons can potentially be used to update the RSP map and adapt the treatment plan. The procedure to measure the dose distribution map can also be used for quality assurance of patient specific treatment plans on standard phantoms before patient treatment. Standard uniform phantoms composed of materials such as polystyrene with well-known composition and proton stopping power can be positioned relative to isocenter, and the treatment plan can be applied using the standard clinical workflow. The measured dose distribution can then be compared with the expectation for the uniform phantom.

Figure 8:
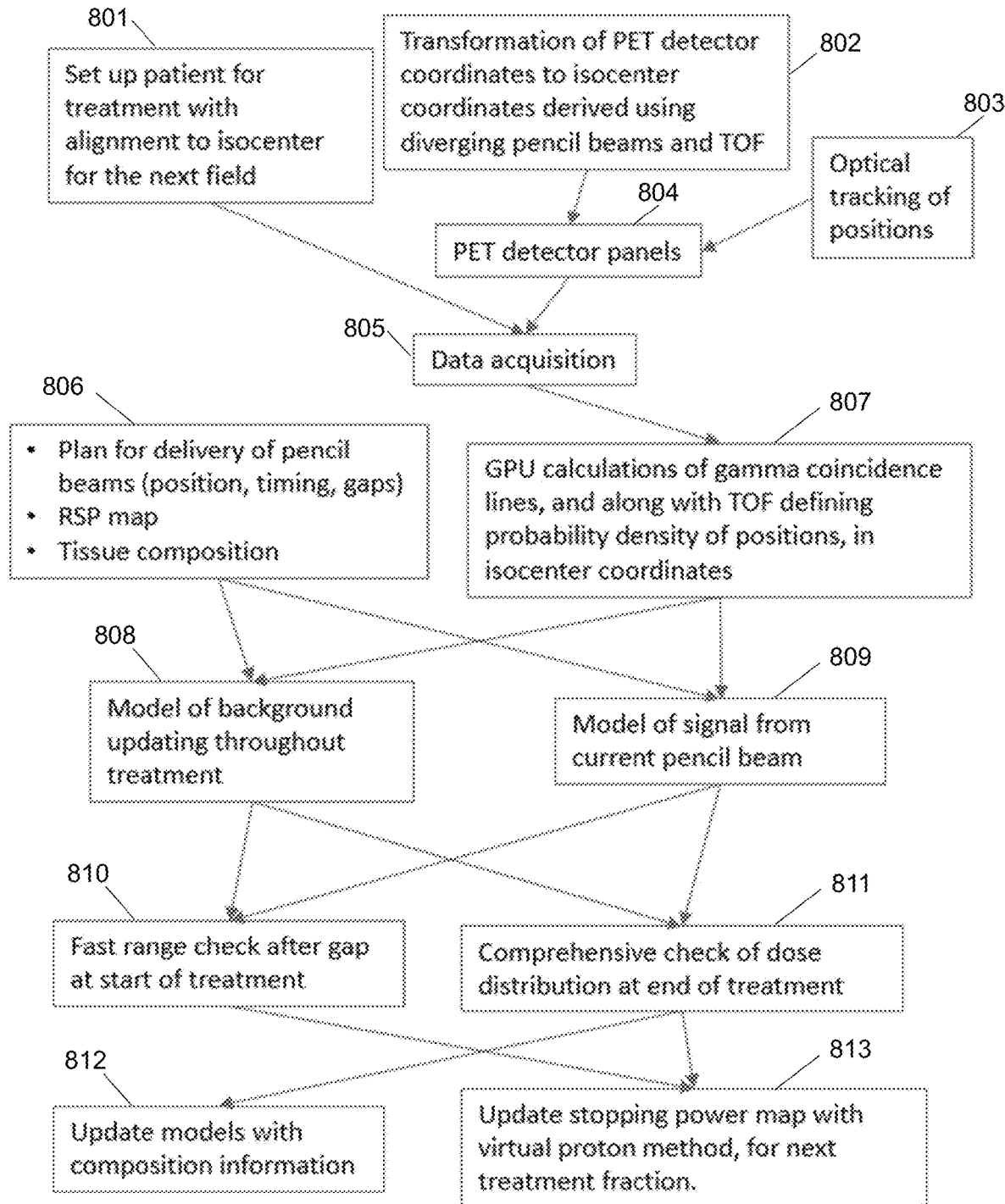
FIG. 8 shows a flow diagram for operating a proton imaging system that enables rapid range checks, dose distribution measurements, and treatment model refinements by utilizing registrations to isocenter, TOF, pencil beam plans, and fast GPU processing, in accordance with an embodiment of the invention.
Figure 9:
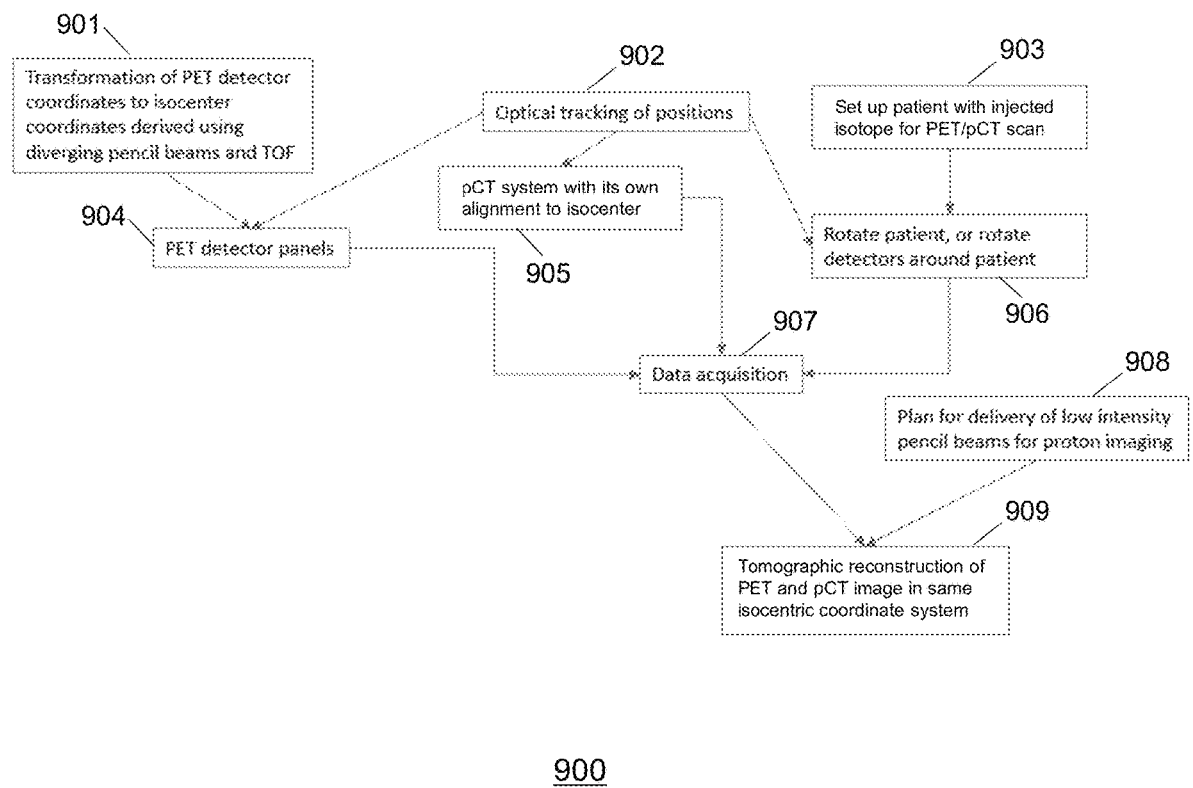
FIG. 9 shows a flow diagram for operating a proton imaging system that transforms PET detector coordinates to isocenter coordinates to enable PET/pCT imaging with the PET and pCT tomographic reconstructions both applied in the same coordinate system, in accordance with an embodiment of the invention.

Flow diagrams (800, 900) in FIGS. 8 and 9 illustrate how the novel proton imaging system that incorporates and/or utilizes PET scanning modules executes computerized data acquisition and image reconstruction steps and interact with the proton beam treatment procedures to produce advantageous clinical capabilities, which were not achievable with conventional (i.e. prior art) proton therapy operation methods. In particular, FIG. 8 shows a flow diagram (800) for operating a proton imaging system that enables rapid range checks/verifications, dose distribution measurements, and treatment model refinements by utilizing registrations to isocenter, TOF, pencil beam plans, and fast GPU processing, in accordance with an embodiment of the invention.

As illustrated in the flow diagram (800) in FIG. 8, in order to accommodate on-the-fly in vivo range verification (e.g. rapid range checks, dose distribution measurements, and treatment model refinements) for proton therapy, the patient is brought to the proton imaging system and is set up for alignment to isocenter for a next treatment field (801). Furthermore, the PET detector coordinates are transformed to isocenter coordinates (802), which are derived using diverging pencil beams and TOF. In the preferred embodiment of the invention, this coordinate transformation to isocenter coordinates utilizes the novel eight-step procedure that has already been described in detail in the present specification. In addition, the proton imaging system also provides optical real-time position tracking (803) of target objects and detectors, as shown in the flow diagram (800).

With the patient properly aligned for the next treatment field in the proton therapy and the PET detector coordinates transformed to the isocenter coordinates, the PET detector panels (804) are utilized to acquire various information (805) from short-lived and/or long-lived positron emitters produced during a proton beam treatment. A scalable graphical processing unit (GPU) server is configured to execute gamma coincidence line and TOF-derived position probability density calculations in isocenter coordinates (807). The acquired data from the PET detector panels include the detection of secondary radiation from the interaction of a proton treatment beam with the target (e.g. a tumor), which provides an opportunity for in vivo range verification by detecting electron-positron annihilation events with scintillators in PET detection modules during the proton beam treatment procedure. Such in vivo range verification techniques may be particularly useful in hypofractionation because the greater number of treatment protons produces a larger signal of secondary radiation.

Continuing with the flow diagram (800) in FIG. 8, the treatment plan (i.e. positions, timing, gaps, etc.) for delivery of pencil beams, the relative stopping power (RSP) map, and tissue composition information (806) are uploaded to a real-time update of a treatment background model (808) and a current pencil beam signal model (809). These models (808, 809) are configured to incorporate outputs of GPU calculations of gamma coincidence line and TOF-derived position probability density calculations dynamically in real time to enable real-time model refinements during the proton therapy process.

With the real-time updates to the treatment background model (808) and the current pencil beam signal model (809), the novel proton imaging system is able to perform a fast range check after gap at the start of each treatment field (810) and provide a comprehensive check of dose distribution at the end of treatment (811), which in turn enables updates and additional refinements to the RSP map with virtual proton methods for the next treatment step (813). Furthermore, the comprehensive check of dose distribution at the end of treatment (811) also enables additional model refinements with composition information (812), as shown in the flow diagram (800) in FIG. 8.

FIG. 9 shows a flow diagram (900) for operating a proton imaging system that transforms PET detector coordinates to isocenter coordinates to enable PET/pCT imaging with the PET and pCT tomographic reconstructions both applied in the same coordinate system, in accordance with an embodiment of the invention. As illustrated in this flow diagram (900), the novel proton imaging system is able to execute machine calculations to transform PET detector coordinates to isocenter coordinates, which are derived using diverging pencil beams and TOF (901). In the preferred embodiment of the invention, this coordinate transformation to isocenter coordinates utilizes the novel eight-step procedure that has already been described in detail in the present specification.

For PET/pCT imaging, the novel proton imaging system also provides optical tracking of positions (902), which can be aligned to isocenter through native alignments by the pCT system (905). The patient is set up with injected isotope for PET/pCT scan (903), and the PET detector panels (904) are utilized for detecting positron emitters after proton beam projections. During the course of PET/pCT scanning, the patient is rotated around the PET detector panels, or the PET detector panels rotate around the patient (906) to capture three-dimensional PET and pCT imaging information (907). After creating and inputting a low-intensity pencil beam delivery plan for proton imaging (908), the novel proton imaging system can execute a computerized tomographic reconstruction of hybrid PET and pCT images in the same isocentric coordinate system (909) from the captured PET and pCT imaging information from the data acquisition stage, as shown in the flow diagram (900) in FIG. 9. The resulting hybrid image is herein referred to as the hybrid PET/pCT (hybrid positron emission tomography and proton CT) scanning, which combines the PET scanner image signatures with the pCT image signatures to provide more accurate proton treatment planning maps for metabolically-active tumors.

Figure 10:
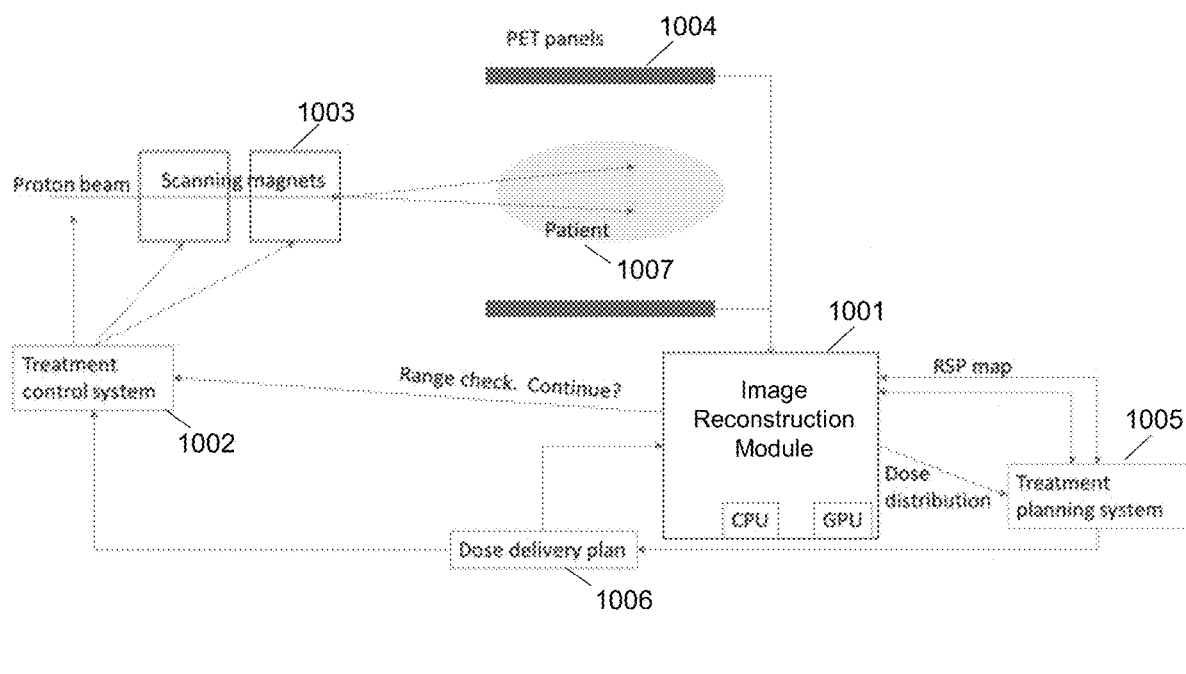
FIG. 10 shows a hardware block diagram of a proton imaging system that enables rapid range checks, dose distribution measurements, and treatment model refinements by utilizing registrations to isocenter, TOF, pencil beam plans, and fast GPU processing, in accordance with an embodiment of the invention.

Moreover, FIG. 10 shows a hardware block diagram (1000) of a proton imaging system that enables rapid range checks, dose distribution measurements, and treatment model refinements by utilizing registrations to isocenter, TOF, pencil beam plans, and fast GPU processing, in accordance with an embodiment of the invention that was previously illustrated and described in conjunction with FIG. 8. In the preferred embodiment of the invention, an image reconstruction module (1001) in the hardware block diagram (1000) is configured to execute one or more software modules that provide transformation of PET detector coordinates to isocenter coordinates derived using diverging pencil beams and TOF, rapid range checks, dose distribution measurements, and treatment model refinements. Typically, the image reconstruction module (1001) incorporates a central processing unit (CPU) and/or a graphics processing unit (GPU) to execute these software modules for the proton imaging system, and is operatively connected to a treatment control system (1002) that controls proton beam steering and scanning magnets (1003) for proton beam delivery to a patient (1007).

The image reconstruction module (1001) is also operatively connected to PET detector panels (1004) to receive positron annihilation coincidence and TOF data for an in vivo range verification during the proton beam treatment process for the patient (1007). The in vivo range verification output from the image reconstruction module (1001) may be a critical factor in machine determination of continuation, stoppage, or modification of the proton beam treatment, based on a current understanding of dose distribution, dose delivery plan(s), and/or treatment plan(s) after the latest dose delivery to the treatment field.

Furthermore, as illustrated in the hardware block diagram (1000), the image reconstruction module (1001) is also operatively connected to a treatment planning system (1005) that provides and updates relative stopping power (RSP) map, tissue composition information, and dose distribution information for each treatment field during the proton therapy process. The updated information from the image reconstruction module (1001) and the treatment planning system (1005) provides real-time refinements and changes to a dose delivery plan (1006), which is integrated into the proton imaging system and commands the treatment control system (1002), as shown in FIG. 10.

Figure 11:
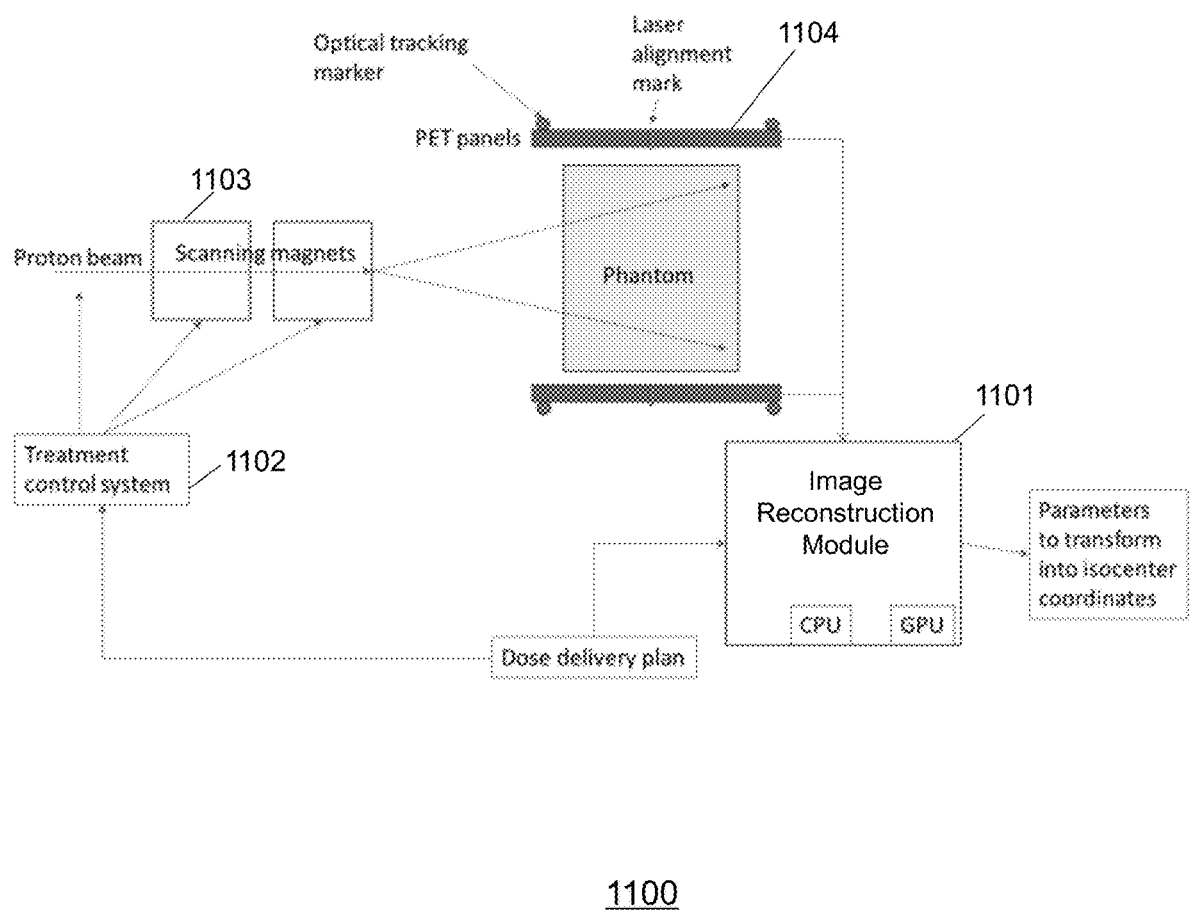
FIG. 11 shows a hardware block diagram of a proton imaging system that transforms PET detector coordinates to isocenter coordinates to enable PET/pCT imaging with the PET and pCT tomographic reconstructions both applied in the same coordinate system, in accordance with an embodiment of the invention.

FIG. 11 shows a hardware block diagram (1100) of a proton imaging system that transforms PET detector coordinates to isocenter coordinates to enable PET/pCT imaging with the PET and pCT tomographic reconstructions both applied in the same coordinate system, in accordance with an embodiment of the invention that was previously illustrated and described in conjunction with FIG. 9. In the preferred embodiment of the invention, an image reconstruction module (1101) in the hardware block diagram (1100) is configured to execute one or more software modules that provide transformation of PET detector coordinates to isocenter coordinates to enable PET/pCT imaging with the PET and pCT tomographic reconstructions both applied in the same coordinate system. Typically, the image reconstruction module (1101) incorporates a central processing unit (CPU) and/or a graphics processing unit (GPU) to execute these software modules for the proton imaging system, and is operatively connected to a treatment control system (1102) that controls proton beam steering and scanning magnets (1103) for hybrid PET/PCT imaging synthesis from a patient.

As shown in the hardware block diagram (1100), the treatment control system (1102) is configured to provide proton beam steering to calibrated locations on an isocenter plane. Furthermore, PET detector panels (1104) incorporate optical tracking markers and laser alignment marks to provide precision image data capture. The image reconstruction module (1101) is operatively connected to the PET detector panels (1104) to receive positron annihilation coincidence and TOF data. Typically, the patient undergoing the PET/pCT image capture process is rotated around the PET detector panels (1104), or alternatively, the PET detector panels (1104) are rotated around the patient to provide a precision three-dimensional tomographic data capture prior to the computerized graphical synthesis of a hybrid PET/pCT image. Then, with a robust set of PET and pCT imaging data acquired from the image data capture process, the image reconstruction module (1101) is able to synthesize a tomographic reconstruction of PET and pCT images in the same isocentric coordinate system. The unique combinatory PET/pCT scanning process, as embodied and described in conjunction with FIG. 9 and FIG. 11, combines the PET scanner image signatures with the pCT image signatures to provide more accurate proton treatment planning maps for metabolically-active tumors.

Various embodiments of the present invention provide several key advantages in proton therapy planning, treatment accuracy, speed, and operational efficiency. One advantage of an embodiment of the present invention is providing a novel proton imaging system that incorporates and/or utilizes positron emission tomography (PET) to enable rapid on-the-fly in vivo range verification for proton therapy by acquiring, deducing, and computing information from short-lived positron emitters produced during treatment. In addition, another advantage of an embodiment of the present invention is providing a novel proton imaging system that incorporates and/or utilizes PET modules to enable a unique combinatory PET/pCT scanning that can provide more accurate maps for proton therapy planning for metabolically-active tumors. Furthermore, another advantage of an embodiment of the present invention is providing a novel method for operating a novel proton imaging system that incorporates and/or utilizes PET modules to improve treatment preparation and procedural efficiencies while reducing operational costs associated with proton therapy.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the claims presented below.

What is claimed is:

1. A method for operating a novel proton imaging system with positron emission tomography (PET) modules to enable rapid on-the-fly in vivo range verifications for proton therapy by utilizing information from short-lived positron emitters produced during a proton beam treatment, the method comprising the steps of:

aligning a patient to an isocenter of a next proton beam treatment field in the novel proton imaging system;

transforming PET detector coordinates to isocenter coordinates, which are derived from diverging pencil beams and a time-of-flight (TOF) technique, wherein relative TOFs of two photons from a positron annihilation provide a measurement of annihilation positions along a line between the two photons;

tracking detectors and a target object in the patient aligned to the isocenter through native alignments provided by the novel proton imaging system;

acquiring positron annihilation coincidence and TOF data from PET detector panels that detect positron emitters produced from a proton beam during treatment, wherein the positron annihilation coincidence and TOF data involves detection of secondary radiation from an interaction of the proton beam with the target object, which provides an opportunity for an in vivo range verification by detecting electron-positron annihilation events with scintillators in the PET detector panels;

executing gamma coincidence line and TOF-derived position probability density calculations in the isocenter coordinates in a scalable graphical processing unit (GPU) of the novel proton imaging system;

creating a treatment plan involving positions, timing, and gaps for delivery of pencil beams, a relative stopping power (RSP) map, and tissue composition information;

uploading the treatment plan to a real-time update of a treatment background model and a current pencil beam signal model executed in the scalable GPU or a central processing unit (CPU) of the novel proton imaging system, wherein the treatment background model and the current pencil beam signal model are configured to incorporate outputs of GPU calculations of the gamma coincidence line and the TOF-derived position probability density calculations dynamically in real time to enable real-time model refinements during the proton beam treatment; and performing a fast range check before the next proton beam treatment field after taking account of the real-time model refinements to the treatment background model and the current pencil beam signal model.

2. The method of claim 1, further comprising the steps of: checking a dose distribution after each proton beam treatment field; updating the RSP map with a virtual proton method for the next proton beam treatment field; and updating the treatment background model and the current pencil beam signal model with new tissue composition information from the step of checking the dose distribution after each proton beam treatment field.

3. The method of claim 1, wherein the step of transforming the PET detector coordinates to the isocenter coordinates from the time-of-flight (TOF) technique involves additional steps of: preparing survey and positioning parameters; utilizing three rotational and three translational parameters for each of two planes with starting values to convert internal detector coordinates to the isocenter coordinates; placing a material block around the isocenter; delivering a set of pencil beams with known steering to isocenter plane and known directions as diverging rays from a focal point; defining a Gaussian distribution for the positron annihilation with pencil beam width and positron diffusion; for each gamma coincidence, drawing a line between gamma hits and finding a probability density of positron annihilation positions, wherein a hit resolution specifies a Gaussian uncertainty transverse to the line and a TOF resolution specifies a Gaussian uncertainty along the line; for each gamma coincidence, calculating a chi-squared value ($\chi^2$) of an overlap between a pencil beam and a coincidence line and summing all chi-squared values of coincidences; and finding rotational and translational parameters that minimize the chi-squared value ($\chi^2$).

4. The method of claim 2, wherein the virtual proton method involves generation of a computer program-deduced and imaginary proton-like particle called a "virtual proton" during PET scanning by the PET detector panels, wherein the virtual proton is configured to mimic a proton particle's characteristics for more accurate proton computer tomography (pCT) or computer tomography (CT) image reconstructions, especially on thick parts of the patient undergoing the proton therapy.

5. The method of claim 4, wherein the virtual proton method further involves a substitution of a proton beam's measured range with virtual protons, which is utilized in an iterative image improvement for CT or pCT reconstruction that adjusts an relative stopping power (RSP) of each voxel to match energy lost by each proton with sums of RSPs along proton paths.

6. The method of claim 5, wherein the virtual proton has a water-equivalent range and a geometrical stopping point of the proton beam as measured by the PET detector panels.

7. The method of claim 6, wherein the virtual proton has a transverse distribution according to a pencil beam's shape.

8. The method of claim 1, wherein the novel proton imaging system with the PET modules comprises an image reconstruction module incorporating the scalable GPU and the CPU, a treatment control system that provides control and steering of the proton beam while incorporating the real-time model refinements, a treatment planning system that provides real-time updates to a dose delivery plan for the next proton beam treatment field, scanning magnets for proton beam projections, and the PET detector panels that detect positron emitters produced from the proton beam during treatment.

9. The method of claim 1, wherein the step of tracking the detectors and the target object in the patient aligned to the isocenter utilizes optical tracking.

10. A method for operating a novel proton imaging system with positron emission tomography (PET) modules to enable a unique combinatory PET and pCT (proton computer tomography) scanning that provides more accurate maps for proton therapy planning for metabolically-active tumors, the method comprising the steps of:

executing machine calculations in a scalable graphics processing unit (GPU) of the novel proton imaging system to transform PET detector coordinates to isocenter coordinates, which are derived from diverging pencil beams and a time-of-flight (TOF) technique, wherein relative TOFs of two photons from a positron annihilation provide a measurement of annihilation positions along a line between the two photons;

tracking detectors and a target object in a patient aligned to an isocenter through native alignments provided by the novel proton imaging system;

injecting isotopes to the patient for the unique combinatory PET and pCT scanning and aligning the patient to the isocenter;

projecting a proton beam and utilizing PET detector panels incorporated in the novel proton imaging system to detect positron emitters after the proton beam is projected on the target object in the patient, wherein the PET detector panels are rotated around the patient, or the patient is rotated around the PET detector panels during this image capture process to obtain a three-dimensional PET and pCT imaging information;

creating and inputting a low-intensity pencil beam delivery plan to the novel proton imaging system;

executing a computerized tomographic reconstruction of hybrid PET and pCT images in a singular isocentric coordinate system, wherein each of the hybrid PET and pCT images combines PET scanner image signatures with pCT image signatures to provide more accurate proton treatment planning maps for the metabolically-active tumors; and displaying the hybrid PET and pCT images for proton treatment planning.

11. The method of claim 10, wherein the step of executing machine calculations to transform the PET detector coordinates to the isocenter coordinates from the time-of-flight (TOF) technique involves additional steps of: preparing survey and positioning parameters; utilizing three rotational and three translational parameters for each of two planes with starting values to convert internal detector coordinates to the isocenter coordinates; placing a material block around the isocenter; delivering a set of pencil beams with known steering to isocenter plane and known directions as diverging rays from a focal point; defining a Gaussian distribution for the positron annihilation with pencil beam width and positron diffusion; for each gamma coincidence, drawing a line between gamma hits and finding a probability density of positron annihilation positions, wherein a hit resolution specifies a Gaussian uncertainty transverse to the line and a TOF resolution specifies a Gaussian uncertainty along the line; for each gamma coincidence, calculating a chi-squared value ($\chi^2$) of an overlap between a pencil beam and a coincidence line and summing all chi-squared values of coincidences; and finding rotational and translational parameters that minimize the chi-squared value ($\chi^2$).

12. The method of claim 10, further comprising a step of utilizing a virtual proton method that involves generation of a computer program-deduced and imaginary proton-like particle called a "virtual proton" during PET scanning by the PET detector panels, wherein the virtual proton is configured to mimic a proton particle's characteristics for more accurate proton computer tomography (pCT) or computer tomography (CT) image reconstructions, especially on thick parts of the patient undergoing the proton therapy.

13. The method of claim 12, wherein the virtual proton method further involves a substitution of a proton beam's measured range with virtual protons, which is utilized in an iterative image improvement for CT or pCT reconstruction that adjusts an relative stopping power (RSP) of each voxel to match energy lost by each proton with sums of RSPs along proton paths.

14. The method of claim 13, wherein the virtual proton has a water-equivalent range and a geometrical stopping point of the proton beam as measured by the PET detector panels.

15. The method of claim 14, wherein the virtual proton has a transverse distribution according to a pencil beam's shape.

16. The method of claim 10, wherein the novel proton imaging system with the PET modules comprises an image reconstruction module incorporating the scalable GPU and a CPU, a treatment control system that provides control and steering of the proton beam while incorporating real-time model refinements, a dose delivery plan with real-time model refinements, scanning magnets for proton beam projections, and the PET detector panels that detect positron emitters produced from the proton beam during imaging.

17. The method of claim 10, wherein the step of tracking the detectors and the target object in the patient aligned to the isocenter utilizes optical tracking.

* * * * *